United States Patent [19]

Schulz et al.

[11] Patent Number: 5,578,723
[45] Date of Patent: Nov. 26, 1996

[54] PROCESS FOR PREPARING CYANURIC ACID BY SEPERATION FROM AN ISOCYANIC ACID/AMMONIA GAS MIXTURE

[75] Inventors: Erich Schulz, Ansfelden; Georg Häubl; Martin Müllner, both of Linz, all of Austria

[73] Assignee: DSM Chemie Linz GmbH, Linz, Austria

[21] Appl. No.: 505,820

[22] Filed: Jul. 21, 1995

[30] Foreign Application Priority Data

Jul. 22, 1994 [AT] Austria ................................. 1454/94

[51] Int. Cl.⁶ ...................... C07D 251/32; C07D 251/60
[52] U.S. Cl. ............................................. 544/192; 544/201
[58] Field of Search ........................................ 544/192, 201

[56] References Cited

U.S. PATENT DOCUMENTS

| | | | |
|---|---|---|---|
| 3,970,742 | 7/1976 | Verstegen | 423/365 |
| 4,110,424 | 8/1978 | Haas et al. | 423/365 |
| 4,182,805 | 1/1980 | Haas et al. | 525/336 |
| 4,187,376 | 2/1980 | Carlson | 544/192 |

FOREIGN PATENT DOCUMENTS

| | | |
|---|---|---|
| 0075612 | 4/1983 | European Pat. Off. . |
| 0124704 | 11/1984 | European Pat. Off. . |
| 2461676 | 7/1975 | Germany . |
| 2841430 | 9/1978 | Germany . |
| 3928556 | 8/1989 | Germany . |
| 3928575 | 3/1991 | Germany . |

OTHER PUBLICATIONS

Chem. Abstr. 115:52900f (1991).
Chem. Abstr. 114:188518z (1991).
Chem. Abstr. 104:88146b (1986).
Chem. Abstr. 102:46723r (1985).
V. V. Dragalov et al., *J. of Anal. and Appl. Pyrolysis*, 25, 311–316 (1993).

*Primary Examiner*—John M. Ford
*Attorney, Agent, or Firm*—Wenderoth, Lind & Ponack

[57] ABSTRACT

A process for preparing cyanuric acid by cooling an isocyanuric acid/ammonia gas mixture having a temperature of 300° to 480° C. to 200°–300° C., whereupon cyanuric acid is separated off and isolated at this temperature in an apparatus suitable for separating solids from gases, and unreacted isocyanuric acid/ammonia gas mixture is recycled or further processed.

10 Claims, No Drawings

PROCESS FOR PREPARING CYANURIC ACID BY SEPERATION FROM AN ISOCYANIC ACID/AMMONIA GAS MIXTURE

A plurality of potential methods of preparation for cyanuric acid are already disclosed by the literature. Thus, cyanuric acid can be prepared for example by the solids pathway, for example by heating urea, the urea being run on a belt through a heated chamber at temperatures between 150° and 300° C. However, a number of byproducts are formed in this process, so that the cyanuric acid thus obtained must be subjected to an acid hydrolysis to achieve commercial quality. A further potential preparation method is the solvent pathway, in which urea is pyrolyzed in a high-boiling solvent. In this case, the solvent used must then be separated off and again an acid hydrolysis must be carried out in order to ensure sufficient quality of the cyanuric acid.

DE 11 08 697 further discloses a process for preparing cyanuric acid in which urea is introduced into a gas stream heated to about 350° to 700° C., the resulting cyanuric acid is separated off from the hot gas and residual urea is recovered. The disadvantage in this process, and in all other processes directly starting from urea, is, however, that the cyanuric acid contains urea impurities which are interferences in various types of further processing, for example for preparing heat-stable fire-retardant pigments.

The object of the present invention is therefore to find a process which gives cyanuric acid, preferably low-urea cyanuric acid, in a simple manner and with high quality.

Unexpectedly, this object was able to be achieved by separating cyanuric acid from an isocyanuric acid/ammonia gas mixture.

The present invention therefore relates to a process for preparing cyanuric acid which comprises cooling an isocyanic acid/ammonia gas mixture having a temperature of 300° to 480° C. to 200°–300°C., separating and isolating cyanuric acid at this temperature by trimerization of the isocyanic acid separating off the solid cyanuric acid from the unreacted isocyanic acid/ammonia gas mixture, and recycling or further processing unreacted isocyanic acid/ammonia gas mixture.

In the process according to the invention, cyanuric acid is separated from an isocyanic acid/ammonia gas mixture by trimerization of the isocyanic acid. The gaseous mixture of isocyanic acid and ammonia necessary for carrying out the process according to the invention should preferably contain 1 to 50% by volume of isocyanic acid. Particularly preferably, a mixture having 3 to 30% by volume of isocyanic acid is used. Suitable isocyanic acid/ammonia gas mixtures are obtained, for example, by urea decomposition, as is carried out for instance in the synthesis of melamine or as described, for example, in EP-A-0 124 704. The temperature of an isocyanic acid/ammonia gas mixture produced, for example, in accordance with EP-A-0 124 704 is about 300° to 480° C. To separate off cyanuric acid, the gas mixture, if appropriate diluted, for cooling, with a carrier gas such as ammonia, nitrogen, argon, helium or carbon dioxide, is introduced into suitable equipment and cooled to 200° to 300° C. Preferably, the temperature is decreased to 230° to 280° C. Suitable equipment which is useful here for cyanuric acid recovery are separation apparatuses which are suitable for separating off solids from gases.

These can be, for example, scrubbing towers, coolers, cyclones, separators such as described in DE 12 27 422, mechanical separation apparatuses such as scraped-surface refrigeration crystallizers or hot gas filters.

Preferably, hot gas filters are used for cyanuric acid separation. Suitable hot gas filters can have various designs for this. Preferably, a cyclone-like hot gas filter having a tangential intake is used which is furnished in the center with filter inserts, for example with ceramic filter candles or ceramic filter felt, with a synthetic cloth resistant to high temperatures, for example a polyimide felt or polysulfone cloth, with sintered metal frits, metal cloth or is furnished with glass frits or glass cloths.

In a preferred embodiment, the isocyanic acid/ammonia gas mixture is first introduced into a gas mixing chamber, for example into a cyclone or a mechanical mixing apparatus, mixed with a coolant gas, such as ammonia, nitrogen, carbon dioxide or another gas inert under the reaction conditions, and the mixed gas thus obtained is introduced into a downstream separation apparatus, preferably into a hot gas filter.

In a particularly preferred embodiment, the gas mixing chamber and the separation apparatus form one unit. In this case, a cooling gas as defined above is introduced through one or more additional inlets into the separation apparatus, preferably into a hot gas filter, the temperature of the coolant gas being chosen so that the overall temperature in the separation apparatus is between 200° and 300° C.

Encrustation of the hot gas filter wall of the mixing chamber wall can be avoided by well-directed introduction of the coolant gas. A further advantage of the coolant gas introduction is that the cooling of the reaction gas need not take place entirely over the vessel wall, so that the wall temperature can be kept somewhat higher than the mixed gas temperature, by which means encrustation is likewise avoided.

If desired, the separation can also be carried out without an additional coolant gas. If no coolant gas is used, the isocyanic acid/ammonia gas mixture is preferably cooled via a cooler before introduction into the separation apparatus.

The degree of separation and the purity of the cyanuric acid in this process is dependent on the temperature, the mixing or rate of mixing between coolant gas and isocyanic acid/ammonia gas mixture, the concentration of isocyanic acid and on the residence time in the gas mixing and/or separation apparatus which is in the range between one millisecond and several minutes, preferably between 0.01 and 20 seconds. These parameters can be varied depending on the desired purity of the cyanuric acid. The cyanuric acid separated off on the filter insert is isolated, for example by knocking off or filter backflushing using gas and, if appropriate, purified, for instance by recrystallization.

The unreacted isocyanic acid/ammonia gas mixture can then be further used, for example unreacted mixed gas can be circulated and, without work-up or purification, can be reused as starting gas for cyanuric acid production. However, unreacted gas mixture can also be introduced into a urea decomposer, for example as carrier gas for urea or as fluidizing gas. A further potential use is, for example, feeding the unreacted gas mixture without work-up or purification steps, after heating to about 300° to 480° C., into a melamine preparation process, and use as starting product for other preparation processes starting from isocyanic acid.

Likewise, the mother liquor obtained by recrystallization of the cyanuric acid can be recirculated several times owing to the low urea content.

The process according to the invention can be carried out both continuously and discontinuously.

In a preferred embodiment of the process according to the invention, the cyanuric acid production is coupled to a melamine preparation process starting from urea decomposition. In this process, urea, for instance as described in EP-A-0 124 704, is decomposed in the fluidized bed to give an isocyanic acid/ammonia gas mixture and some of the gas mixture or all of the gas mixture after leaving the decomposition equipment is introduced into one of the abovementioned types of separation equipment, preferably into a hot gas filter. At the same time, a coolant gas is introduced through one or more additional inlets. Cyanuric acid is separated off under the abovementioned conditions, the unreacted isocyanic acid/ammonia gas mixture which also contains the coolant gas is then fed again to the melamine preparation process, in which case the gas mixture can either be introduced into the decomposer, or the gas mixture is heated to 300° C. –480° C. and introduced into a melamine contact furnace. This coupled procedure considerably increases the economic efficiency of the process according to the invention.

By means of the process according to the invention, cyanuric acid can be prepared in a simple manner in high purity which is at least 90% and sometimes above 95%.

EXAMPLE 1

Into a hot gas filter having a volume of 3 1 which comprises a heatable jacketed vessel which is conically tapered downwards, a heatable cover into which is screwed a ceramic filter insert having a pore diameter of 15 μm (Schuhmacher company), a discharge apparatus at the bottom end and 2 slightly offset gas inlets at the upper end, were introduced tangentially 2.2 m$^3$ (S.T.P.) of pyrolysis gas (prepared by thermal decomposition of urea by analogy with EP-A-O 124 704) at a temperature of 380° C. in the course of 1.5 hours together with 3 m$^3$ (S.T.P.) of a nitrogen stream having a temperature of 200° C., where the wall temperature of the hot gas filter was 270° C.

The isocyanic acid concentration in the hot gas filter was 6.8% by volume, the remainder was ammonia and nitrogen. The temperature in the hot gas filter was kept at 270° C. 60 g of solids which was composed of 92.4% cyanuric acid, 0.6% ammelide, 1.3% ammeline, 6.3% melamine and 0.0029% urea were isolated from the filter.

30 g of solids were recrystallized in water, by which means cyanuric acid having a purity of >99.8 and a urea content of <10 μg/g was obtained.

Analogously to Example 1, further studies were carried out with altered parameters.

The results and the parameters are summarized in Table 1.

The temperature of the pyrolysis gas (PG) here was always 380° C., the temperature of the coolant gas stream (CG) was 200° C., and nitrogen ($N_2$), ammonia ($NH_3$) and carbon dioxide ($CO_2$) were used as coolant gas.

In Examples 2, 3, 9, 10 and 11, ceramic filter candles (Schuhmacher company, type: Dia-Schumalith F-40 having an internal diameter of 28 mm and an outer diameter of 60 mm and corrugated surface) were used and in the remaining examples polyimide filters were used (Lenzing company, type: P-84 needle felt, filter dimensions 250×28 mm, filter surface area: 220 cm$^2$).

In addition, the following abbreviations are used:
Operating time: OT
Wall temperature: WT
Isocyanic acid concentration: IC
Mixed gas temperature in the hot gas filter: MT
Amount of solids separated: SS
Content of cyanuric acid after recrystallization: CaR
not determined: nd
Content of cyanuric acid before recrystallization: CbR
Urea content before recrystallization: UbR
Urea content after recrystallization: UaR

TABLE 1

| Example | PG (m$^3$ (S.T.P.)) | CG/type (m$^3$ (S.T.P.)/h) | TO (min) | WT (°C.) | IC (vol %) | MT (°C.) | SS (g) | CbR (%) | UbR (%) | CaR (%) | UaR (μg/g) |
|---|---|---|---|---|---|---|---|---|---|---|---|
| 2 | 2.45 | 2.0/N$_2$ | 92 | 230 | 7.3 | 242 | 93 | 93.9 | 0.280 | >99.9 | <20 |
| 3 | 10.80 | — | 158 | 240 | 10.3 | 260–276 | 185 | 95.6 | 0.100 | >99.8 | 15 |
| 4 | 2.35 | 2.0/N$_2$ | 88 | 230 | 5.0 | 240 | 55 | 93.8 | 0.200 | n.d. | n.d. |
| 5 | 2.77 | 2.4/NH$_3$ | 79 | 230 | 4.8 | 251 | 44 | 92.1 | 0.075 | n.d. | n.d. |
| 6 | 4.12 | 1.2/CO$_2$ | 79 | 270 | 7.0 | 251 | 45 | 92.1 | 0.120 | n.d. | n.d. |
| 7 | 26.60 | — | 605 | 250 | 10.5 | 270–290 | 513 | 91.0 | 0.155 | n.d. | n.d. |
| 8 | 37.60 | 2.4/NH$_3$ | 556 | 250 | 3.0 | 250–260 | 103 | 91.8 | 0.100 | n.d. | n.d. |

Other studies were carried out in a similar manner to Example 1 with the difference that the pyrolysis gas was cooled without use of coolant gas via a cooler before introduction into the hot gas filter.

Pyrolysis gas temperature after cooler: TaC
Time for introduction into the hot gas filter: IT

| Example | PG (m$^3$ (S.T.P.)) | TaC (°C.) | IT (min) | WT (°C.) | IC Vol % | MT (°C.) | S (g) | CbR % | UaR % |
|---|---|---|---|---|---|---|---|---|---|
| 9 | 7.1 | 280 | 160 | 230 | 14.1 | 260–280 | 265 | 85.0 | 0.900 |
| 10 | 8.1 | 290 | 157 | 250 | 14.6 | 270–285 | 190 | 92.5 | 0.042 |
| 11 | 7.9 | 280 | 162 | 240 | 14.3 | 270–285 | 152* | 96.2 | 0.013 |

*152 g of crystalline solids and 70 g of hard crust containing 79.3% cyanuric acid were isolated from the separation apparatus.

What we claim is:
1. A process for preparing cyanuric acid which comprises cooling an isocyanic acid/ammonia gas mixture having a temperature of 300° to 480° C. to 200°–300° C., and isolating cyanuric acid at this temperature by trimerization of the isocyanic acid and separating off the solid cyanuric acid from the unreacted isocyanic/ammonia gas mixture, and recycling or further processing unreacted isocyanic acid/ammonia gas mixture.

2. The process as claimed in claim 1, wherein the isocyanic acid concentration in the isocyanic acid/ammonia gas mixture is 1–50% by volume.

3. The process as claimed in claim 1, wherein the isocyanic acid concentration in the isocyanic acid/ammonia gas mixture is 3–30% by volume.

4. The process as claimed in claim 1, wherein the isocyanic acid/ammonia gas mixture is obtained by thermal decomposition of urea.

5. The process as claimed in claim 1, wherein cyanuric acid is separated off at 230°–280° C.

6. The process as claimed in claim 1, wherein cyanuric acid is separated off in a hot gas filter.

7. The process as claimed in claim 1, wherein cyanuric acid is separated off in a cyclone-like hot gas filter having a tangential intake, which filter is furnished in the center with filter inserts.

8. The process as claimed in claim 1, wherein the isocyanic acid/ammonia gas mixture is mixed with coolant gas in a gas mixing chamber, the mixed gas thus obtained is introduced into a hot gas filter and cyanuric acid is separated off.

9. The process as claimed in claim 1, wherein the isocyanic acid/ammonia gas mixture is mixed in the hot gas filter with coolant gas which is introduced through one or more further inlets.

10. A process for preparing cyanuric acid coupled with a melamine preparation process starting from urea decomposition, which comprises decomposing urea in a fluidized bed at 300°–480° C. to give an isocyanic acid/ammonia gas mixture, passing some of the gas mixture or all of the gas mixture after it leaves the decomposition equipment into a separation apparatus, and, if appropriate with simultaneous introduction of a coolant gas, separating off cyanuric acid at a temperature of 200°–300° C., whereupon the unreacted isocyanic acid/ammonia gas mixture is either reintroduced into the decomposition equipment or is heated to a temperature of 300°–480° C. and is processed to give melamine in a melamine contact furnace or is used as starting product for other preparation processes starting from isocyanic acid.

* * * * *